United States Patent

Gautsch et al.

Patent Number: 5,618,399
Date of Patent: Apr. 8, 1997

[54] COMB ELEMENTS ROTATING IN POSITION TO PLACE SELECTED SLIT ARRAYS IN THE GEL OF AN ELECTROPHORESIS AGAROSE GEL TRAY, PARTICULARLY AS ALSO SERVE AS SPACERS BETWEEN STACKED TRAYS

[76] Inventors: James W. Gautsch, 451 S. Grenados Ave., Solana Beach, Calif. 92075; Syed F. H. Rehan, 635 Cabezone Pl., Vista, Calif. 92083

[21] Appl. No.: 595,648

[22] Filed: Feb. 2, 1996

Related U.S. Application Data

[63] Continuation-in-part of Ser. No. 377,866, Jan. 25, 1995, Pat. No. 5,514,255.
[51] Int. Cl.⁶ ..................... G01N 27/26
[52] U.S. Cl. .............. 204/620; 204/615; 204/465
[58] Field of Search ............. 204/465, 456, 204/606, 615, 619, 620; 132/126, 137, 139, 141, 142

[56] References Cited

U.S. PATENT DOCUMENTS 2,507,373  12/1947  Finkelstein ............... 132/142
5,337,765  8/1994  Wong ...................... 132/142

Primary Examiner—Kathryn L. Gorgos
Assistant Examiner—Alexander Noguerola
Attorney, Agent, or Firm—Fuess & Davidenas

[57] ABSTRACT

A spacer-comb element including (i) a longitudinal central axis and (ii) three or more, preferably four, teeth arrays radially extending about the central axis and extending along a length thereof, serves to emplace arrayed slit apertures within flat sheets of a gel state material that is itself suitable to receive samples upon which electrophoresis may be performed. The spacer-comb element is placed between the sidewalls of, and engaged by, a tray holding the gel material in a central reservoir so that the teeth of only a selected one array extend downwards into the tray. An opposite, upwards-extending, teeth array engages the underside of an overlying tray, preferably at an optional complimentary groove feature on the tray's underside, so as to support the tray. A stack of trays and intervening spacer-comb elements is used as a system and in a method for preparing multiple trays of a gel state material, normally an agarose gel, all in one step at the same time, each prepared gel having arrayed slit apertures of selected number(s) and at selected location(s).

10 Claims, 1 Drawing Sheet

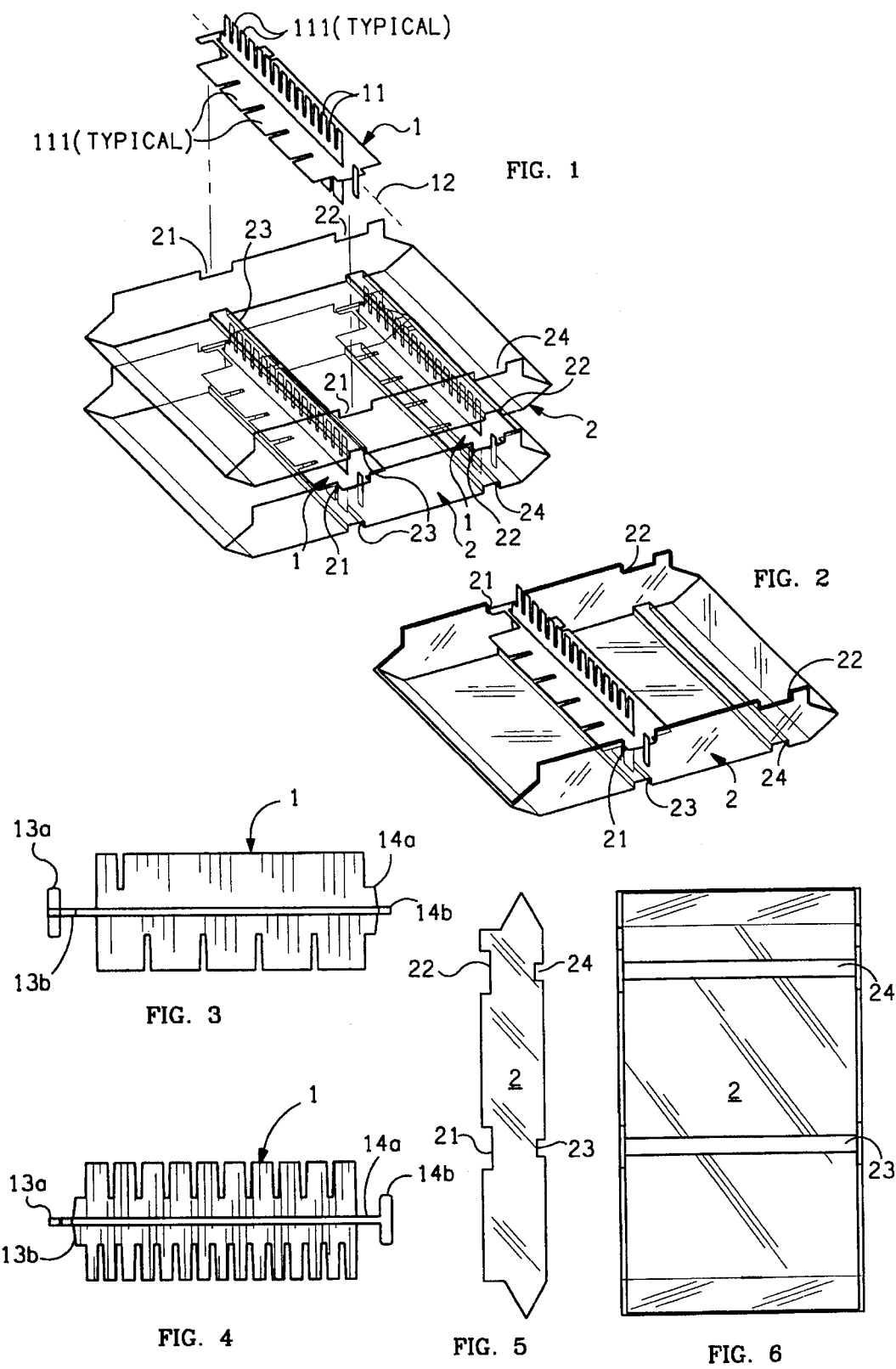

COMB ELEMENTS ROTATING IN POSITION TO PLACE SELECTED SLIT ARRAYS IN THE GEL OF AN ELECTROPHORESIS AGAROSE GEL TRAY, PARTICULARLY AS ALSO SERVE AS SPACERS BETWEEN STACKED TRAYS

REFERENCE TO A RELATED PATENT APPLICATION

The present patent application is a continuation-in-part of U.S. patent application Ser. No. 08/377,886 filed on Jan. 25, 1995, for VERTICALLY STACKED TRAYS OVERFLOWING LIQUID CONGEALING INTO ELECTROPHORESIS GEL, AND OPTIONAL COMBINATION SPACER-COMBS BETWEEN THE TRAYS, issued as U.S. Pat. No. 5,514,255. The predecessor application and patent is to the selfsame inventor James Gautsch who is a co-inventor of the present application. The content of the related patent application and patent is incorporated herein by reference.

BACKGROUND OF THE INVENTION

1. Field of the Invention

The present invention generally concerns the preparation of gels, typically agarose gels, that are suitable to receive samples upon which electrophoresis is performed.

The present invention particularly concerns the placement of precision arrays of slits in trays of gels, typically agarose gels, that are suitable to receive samples upon which electrophoresis is performed.

The present invention still more particularly concerns a spacer-comb element—particularly as is useful in a special apparatus and a method for the easy simultaneous preparation of multiple trays of gels, typically agarose gels, that are suitable to receive samples upon which electrophoresis is performed—that is useful in conveniently placing arrayed slits in the gel of a gel tray.

2. Description of the Prior Art

Agarose gel electrophoresis is commonly used for both analytical and preparative separation of DNA fragments. Standard agarose gels separate DNA fragments from≈0.1 to 25 kilobases, or kb, whereas pulsed-field agarose gels resolve molecules from≈10 to >2000 kb. Descriptions of standard and pulsed-field agarose gel electrophoresis, as well as parameters affecting resolution of large DNA fragments, are presented in standard textbooks. At least three different protocols employing agarose gels to prepare DNA fragments are known. An agarose gel has the properties of an electric circuit.

One leading protocol for using agarose gel electrophoresis as a simple and highly effective method for the separation, identification and purification of ≈0. to 25 kb DNA fragments can be divided into three stages. First, a gel is prepared with an agarose concentration appropriate for the size of DNA fragments to be separated. Second, the DNA samples are loaded into the sample wells and the gel is run at a voltage and for a time period that will achieve optimal separation. Third and finally, the gel is stained or, if ethidium bromide has been incorporated into the gel and into the electrophoresis buffer, visualized directly upon illumination with ultraviolet (UV) light.

In order to conduct agarose gel electrophoresis, an agarose gel must be prepared upon a suitable substrate, and made ready to receive the DNA fragments to be separated, normally so as to receive these DNA fragments into each of an arrayed succession of small wells in the form of slits in the agarose gel. This preparation is the subject of the present invention.

2.1 Historical Preparation of Electrophoresis Gels

Preparation typically commences by sealing the edges of a clean, dry, glass plate (or the open ends of the plastic tray supplied with the electrophoresis apparatus) with autoclave tape so as to form a mold. An electrophoresis buffer (usually 1×TAE or 0.5×TBE) sufficient in amount so as to fill the electrophoresis tank and to prepare a gel is prepared. An amount of powdered agarose is added to a measured quantity of electrophoresis buffer in an Erlenmeyer flask or a glass bottle with a loose-fitting cap. The same batch of electrophoresis buffer is used in both the electrophoresis tank and the gel.

The neck of the Erlenmeyer flask is loosely plugged. The slurry of powdered agarose and buffer is heated in a boilingwater bath or a microwave oven sufficiently so as to permit all of the grains of agarose to dissolve. The dissolved solution is cooled to 60° C., and if desired, ethidium bromide is added.

The liquid is poured into the mold and permitted to cool to produce a gel. The higher the concentration of agarose, the quicker the gel hardens.

In order to produce slits, or wells, in the gel—into which wells samples undergoing electrophoresis will be inserted—a separate comb is typically positioned 0.5–1.0 mm above the glass plate, or base of the mold. The teeth of the comb form a series of linearly aligned wells when the liquid agarose solution is added to the mold. When the comb is properly manually positioned above the plate, or base of the mold, then it is typically supported on its outer teeth so that its inner teeth will automatically lifted slightly above, and clear of, the plate. The present invention will be seen to particularly involve improvements to this comb.

After the gel is completely set both the comb and autoclave tape are carefully removed, and the gel is mounted in the electrophoresis tank. Just enough electrophoresis buffer is added so as to cover the gel to a depth of about 1 mm.

A sample of DNA is mixed with a desired gel-loading buffer. This mixture is slowly loaded into the slits, or wells, of the submerged gel using a disposable micropipette, an automatic micropipettor or a pasteur pipette. Electrophoresis is then performed.

This prior art procedure for the production of a tray of gel, typically an agarose gel, is (i) labor intensive, and thus (ii) expensive, (iii) tedious, and (iv) ill-adapted to efficiencies of scale because a large number of gel trays are roughly more difficult to make than is a single gel tray in proportion to the numbers thereof.

Moreover, the slits, or wells, that are formed in the gel may be of improper or inconsistent depth in accordance that the manual alignment procedure induces errors.

Admittedly, separation by process of electrophoresis of such samples as are later inserted within the slits, or wells, of the gel may accord a certain registration upon viewing (or photographing) that is based on the innate visual properties of the samples. However, it is illogical, and of dubious soundness as a scientific procedure, that successive gels upon which electrophoresis is performed should not be, insofar as is possible, identical. Although exact chemical identity may not be possible between successive gels that are not simultaneously prepared (the present invention will be seen to greatly abet simultaneous preparation of multiple gels), any significant mechanical variation in gel size and thickness, and the locations and depths of the slits (wells) locations in the gels should be, insofar as is possible, strictly avoided.

Presently, the greatest problem occurs with adjusting the depths of the slits should a one, predetermined, slit depth offered by current equipments prove unsatisfactory. Precision machined combs that are matched to gel trays, and which are accurately positionable thereon by action of tongues and grooves, are known. Variable numbers of slits, or wells, may be selected (in accordance that the comb has a greater, or smaller, number of teeth). However, these slits, or wells, are necessarily of differing depths in gels of various thicknesses. Sometimes it is sufficient, and desired, that all slits, or wells, in all of a number of gels should be formed to be at a uniform height, nominally 1 mm, above the base of the tray at their lowermost extension. The present precision gel combs accord this capability. However, it is sometimes desirable to leave a greater thickness below the wells. The present system does not support of creating wells having a variably selectable depth, which depth may, nonetheless to being variably selectable, be uniform from gel tray to gel tray across as large number of gel trays.

2.2 Concurrent Preparation of Multiple Agarose Gels for Electrophoresis in Accordance with the Invention of the Related Application In accordance with these limitations and problems of the prior art, the related application teaches an apparatus and a method for the simultaneous production of a large number of agarose gel trays complete with precision located and arrayed slits, or wells. These trays are reliably, easily and inexpensively made. The numbers and three-dimensional positions—especially the extent above gel tray bottom—of the slits, or wells, which are formed in the gel are, nonetheless to being variably selectable, precisely controllable. "Precisely controllable" means that two or more gel trays may each be made at separate times to custom mechanical characteristics that are effectively identical. As an arbitrary example, a gel tray having the physical dimensions of 20 cm by 30 cm bed dimension containing a gel of a (relatively thick) 7 mm perforated at exactly 10 slits of 1.0 mm each at positioned 1 cm from a short side wall, each slit to a (relatively high) 1.5 mm above the base of the tray can be repetitively reliably made, and re-made. This precision over a range of dimensions—especially as relate to the vertical extent of the slits above the base of the gel tray—is effectively impossible with the historical apparatus, and procedures.

The related invention and application thus concerns an apparatus and method for greatly (i) reducing the labor, and thus (ii) reducing the expense, (iii) reducing the tedium, and (iv) enhancing the efficiency of producing large numbers of gel trays by virtue of introducing economies of scale to the entire process.

In the related invention, multiple trays of an identical special configuration are vertically stacked, one atop the next. Each tray has and defines a shallow reservoir and an overflow port from the reservoir. The successive stacked trays are in a same top-bottom orientation, but are typically and preferably reversed end-to-end one tray to the next.

A liquid, normally a hot agarose solution, is then poured into the reservoir of the top tray. The liquid fills this top tray's reservoir to a predetermined depth, and then overflows this top tray through its overflow port, flowing downward into a next lower tray in the stack. The liquid continues to overflow each tray in turn, cascading downwards from tray to tray as each tray is filled to a uniform even level and ultimately reaching the bottom tray of the stack. The liquid that is within each tray is permitted to gel, thereby forming a gel state material that is suitable to receive samples upon which electrophoresis may be conducted.

The process may optionally be abetted by the insertion of combination spacer and toothed comb, or spacer-comb, elements between the stacked trays. In its spacer function each element serves to (i) space apart the stacked trays so that any untoward and undesired wicking of liquid onto the underside of an overflowing tray is more effectively precluded. In its simultaneous comb function, each element has and presents teeth that extend downwards into the reservoir of an underlying tray, thereby to (ii) prevent the liquid from occupying an array of small volumes in the reservoir of the tray. By this action, when the liquid gels then an array of small slits, or wells, will have been formed in the gel state material. Samples upon which electrophoresis is performed may be later be inserted into these arrayed wells.

The present invention will shortly be seen to concern still further improvements to these spacer-comb elements.

In particular detail of construction, each tray is preferably substantially in the shape of a nearly flat typically rectangular parallepiped body having and presenting a shallow trough, or reservoir. A tray is typically, and preferably, made from ultraviolet (UV) transparent acrylic plastic. Each tray is suitably sized and configured so as to be vertically stacked with a number of other trays in a vertical stack, and may be so aided by the optional inclusion of interlocking detentes, normally at the tray corners. The trays need not be, and are not normally, stacked in the same orientation in the stack, but are instead reversed 180° in direction along their long axis from one tray to the next.

Each tray has (i) a substantially flat interior reservoir, (ii) an overflow outlet from which liquid received into the reservoir will flow out of the reservoir when a predetermined liquid level is reached in the reservoir, and (iii) a top opening to the reservoir located so that it may be disposed in position below the overflow outlet of any immediately overlying tray in the vertical stack of trays. The trays are commonly rectangular.

The overflow outlet may be in the form of any of (i) a lip, less than the normal height of the sides of the reservoir, that is normally slightly indented from a side of the rectangular tray, (ii) a baffle of predetermined height, less than the walls of the reservoir, that protects a hole that is normally located in a one corner of the reservoir, (iii) a standpipe, typically spaced apart slightly from the sides of the reservoir normally near a corner, that is of lessor height than the walls of the reservoir, or (iv) any mechanical construction that simply permits the reservoir of the tray to fill to a predetermined level and then directs the overflowing fluid downwards from the tray in a preset course.

The top opening of the tray's reservoir may be coextensive with the entire reservoir of the tray itself, or may be more constrained in accordance that the tray's reservoir may be partially covered by an optional cover, and/or an optional spacer-comb element—which elements may have, in some of their configurations, the effect of covering a portion of the tray's reservoir. Regardless of its extent, a top opening to the reservoir is positioned so as to fall in position directly below the egress of overflowing fluid from a superior tray in the vertical stack. The trays so configured permit liquid poured in the topmost tray of a stack to cascade downwards from tray to tray, filling each tray to a predetermined depth, in a similar manner of a classic water clock.

In another of its aspects, the related invention contemplated an apparatus usable so as to prepare from a liquid, normally an agarose gel solution, a flat sheet of a gel state material having and defining an array of wells, wherein each well is suitable to receive a sample upon which electrophoresis may be performed.

The apparatus included (i) a tray having a base and sides defining a substantially flat and shallow interior reservoir; and (ii) a "comb" member at least partially overlying the reservoir of the tray. To the extent the comb member so overlaid the reservoir of the tray it forms a partial cover thereto. The comb member had linearly arrayed teeth in the manner of a comb. The comb member typically and preferably served to interact with mechanical features of the order of guides, or detentes, on the tray in order that it and its teeth may be easily precisely located relative to the tray and the tray's reservoir.

The teeth of the comb member extended, when the comb member was in position overlying the tray and its reservoir, downward into the reservoir. An array of small volumes—corresponding to the volumes occupied by the teeth—was therein established within the reservoir by the teeth of the comb member. No liquid poured or otherwise entered into the tray's reservoir could enter into these volumes because they were occupied by the teeth of the member.

As previously stated, the present invention will shortly be seen to concern still further improvements to these comb members, or spacer-comb elements.

According to the construction of such an apparatus, when a liquid material is poured into the tray while the comb member is in its typically precise location at least partially overlying the tray's reservoir, and after the liquid material is permitted to gel, then a separation of the comb member from the tray left an array of precisely located voids in the gel state material located within the tray's reservoir. These arrayed voids, or slits, or wells, were of suitable size, depth and placement so as to receive samples upon which electrophoresis is performed.

Both aspects of the related invention may beneficially be combined, permitting the quick and efficient preparation of a number of trays, each of which trays contains a gel state material replete with arrayed wells, all at the same time.

SUMMARY OF THE INVENTION

The present invention contemplates a spacer-comb element that is suitable to emplace any selected one of several pluralities—normally three or more and most commonly four such pluralities differing in number—of arrayed slit apertures within flat sheets of a gel state material that is itself suitable to receive samples upon which electrophoresis may be performed. The spacer-comb element may be particularly conveniently used in a system and in a method for preparing multiple trays of a gel state material, normally an agarose gel, all in one step at the same time.

Nonetheless to being prepared (i) all at the same time, and (ii) by the selective use of multiple identical (1) trays and (2) spacer-comb elements of a single apparatus, or system, the arrayed slit apertures within the gels of the several trays may be of (a) a selectively predetermined number, and in (b) selectively predetermined positions, each of which may be selectively individually different from some or all of the arrayed slit apertures within the other trays. Therefore, and nonetheless to being made at the same time, the arrayed slit apertures within the gels of all the several trays semi-custom in each of (i) number and (ii) position, one tray to the next.

This ability to make semi-custom electrophoresis gel arrays from the common parts of a common system is based on the new spacer-comb element of the present invention.

In its preferred embodiment, the new spacer-comb element includes a longitudinal central axis and three or more arrays radially extending about the central axis and extending along a length thereof. Each of the arrays includes a number, normally a different number, of arrayed teeth. These arrayed teeth are suitable to extend into, and to emplace correspondingly arrayed slit apertures within, flat sheets of a gel state material that is itself suitable to receive samples upon which electrophoresis may be performed.

There are preferably four such radially extending arrays. Each such array preferably has a different number of teeth than are present in any other of the arrays. There are normally 2, X, 2X and 3X teeth respectively in the preferred four arrays where X is an integer number greater than 2, and where X most commonly equals 5 or 6.

The preferred four radially extending arrays are preferably evenly angularly located each at 90° of angular separation circumferentially around the central axis.

Further in accordance with the present invention, a spacer-comb element so constructed is cooperatively interactive with a tray that both (i) has and defines a central reservoir and sides, and (ii) contains a flat sheet of the gel state material that is suitable to receive samples upon which electrophoresis is performed. The spacer-comb element and the tray are so cooperatively interactive by virtue of incorporating engagement features.

The engagement features of the spacer-comb element are aligned with the central axis and extend beyond each and all of the four radially extending arrays at each end region of the 10 central axis. These spacer-comb element engagement features serve to engage an opposing two sides of the tray while the spacer-comb element is set on top of the tray spanning the width thereof between the opposing sides. The engagement is saccade in that the spacer-comb element is stably held with the teeth of one only of its four arrays extending downward into the central reservoir of the tray, and into the gel material contained therein.

The spacer-comb element engagement features are preferably formed as (i) a first tab region that is aligned with the central axis at each end region thereof, that extends beyond each of the four radially extending arrays, and that is co-planar with two of the four arrays, and as a (ii) second tab region that is aligned with the central axis at each end region thereof, that extends beyond each of the four radially extending arrays, and that is co-planar with a remaining two of the four arrays. Clearly the first tab region is perpendicular to the second tab region.

Notably, the order of the tab regions is reversed at the two end regions of the central axis of the spacer-comb element. This reversal accords that when the spacer-comb element is set on top of the tray spanning the width thereof between the opposing sides at a first side-to-side offset then the first tab regions will engage the sides of the tray, and as a consequence thereof a first selected one of the four arrays will extend downward into the central reservoir of the tray, and into the gel material contained therein. Alternatively, when the spacer-comb element is set on top of the tray spanning the width thereof between the opposing sides at a second side-to-side offset, then the second tab regions will engage the sides of the tray, and as a consequence thereof a second selected one, perpendicular to the first selected one, of the four arrays will extend downward into the central reservoir of the tray, and into the gel material contained therein. The tab regions engaging the sides of the tray are in particular perpendicular to the radially extending array that extends downward into the central reservoir of the tray, and into the gel material contained in the reservoir. Basically, any one of the four arrays can be selected to extend downward into the reservoir of the tray, and into the gel contained in the reservoir.

The tray also, additionally, optionally has and presents engagement features. These features are preferably in the form of one or more pairs of small recesses, or notches, located in the top edges of opposing sidewalls. These recess pairs are complimentary in shape to the tab regions of the spacer-comb elements. Each pair or recesses serves to both (i) to engage, and (ii) to precisely position in all axis, a single spacer-comb element relative to the tray, and relative to the gel contained therein. Several pairs of recesses may simultaneously engage and position a corresponding number of spacer-comb elements which spacer-comb elements—although physically identical—are commonly typically rotated so that a different one of its several (4) arrays of teeth is extending downward into the reservoir of, and into the gel within, the tray.

Accordingly, a number of identical comb elements in accordance with the present invention can cooperatively interact with a number of identical trays that are suitably used to prepare in each tray from a liquid material poured into the tray a flat sheet of a gel state material suitable to receive samples upon which electrophoresis may be performed. In this application each tray includes (i) a tray body suitably vertically stacked with a number of other trays in a vertical stack, the tray body having and defining a substantially flat interior reservoir, (ii) an overflow outlet from which liquid received into the reservoir will flow out of the reservoir when a predetermined liquid level is reached in the reservoir, and (iii) a top opening located so that it may be disposed in position below the overflow outlet of any immediately overlying tray in the vertical stack of trays.

The radially extending arrays of the comb elements so interacting with these identical trays have the preferred four radially extending arrays each located at 90° of angular separation circumferentially around the central axis. The engagement features of the comb interact with the sides of the tray so as to hold and to maintain the teeth of one only of the four arrays extending downward into the central reservoir of the tray, and into the gel material contained therein. However, the same engagement features also serve to hold and maintain the 180° oppositely directed array extending upwards from the tray in a position suitable to serve as a spacer and as a rest for an immediately overlying tray in the vertical stack of trays.

By this construction the comb elements with their engagement features serve not only as combs to emplace slit apertures in the gel within an underlying tray, but also as spacers and as rests to support an overlying tray. They are thus commonly called "spacer-comb elements" in this application.

These and other aspects and attributes of the present invention will become increasingly clear upon reference to the following drawings and accompanying specification.

BRIEF DESCRIPTION OF THE DRAWINGS

FIG. 1 is an exploded diagrammatic perspective view of a preferred embodiment of a spacer-comb element in accordance with the present invention as may particularly be fit to a complimentary tray otherwise suitable (i) to receive an agarose gel solution, and, if desired, (ii) to stack.

FIG. 2 is a diagrammatic perspective view of the preferred embodiment of a spacer-comb element in accordance with the present invention fit to the complimentary tray previously seen in FIG. 1.

FIG. 3 is a top plan view of the preferred embodiment of a spacer-comb element in accordance with the present invention previously seen in FIGS. 1 and 2.

FIG. 4 is a side plan view of the preferred embodiment of a spacer-comb element in accordance with the present invention previously seen in FIGS. 1-3.

FIG. 5 is a side plan view of the complimentary tray, usable with the preferred embodiment of a spacer-comb element in accordance with the present invention, that was previously seen in FIGS. 1 and 2.

FIG. 6 is a top plan view of the complimentary tray, usable with the preferred embodiment of a spacer-comb element in accordance with the present invention, that was previously seen in FIGS. 1, 2 and 5.

DESCRIPTION OF THE PREFERRED EMBODIMENT

An exploded diagrammatic perspective view of a preferred embodiment of a spacer-comb element 1 in accordance with the present invention is shown in FIG. 1. The spacer-comb 1 may particularly be fit to a complimentary tray 2, normally at the locations of one or more pairs 21, 22 of opposed recesses (i.e., recess pairs 21, 22) that are formed into the top edges of opposed sidewalls of the tray 2. The tray 2 is suitable to receive an agarose gel solution (not shown) that is simply poured into the tray as a liquid, and that subsequently collects and gels in the bottom of the tray including in position about the (then) downward-extending arrayed teeth 11 of the spacer-comb element 1. When the gel-forming liquid, normally agarose liquid, has gelled, then the spacer-comb element 1 is withdrawn under force of the fingers, leaving an array of cavities, voids, or slits in the gel (not shown). It is into these slits that DNA sample and like samples (not shown) are inserted before undergoing separation by process of electrophoresis.

It is previously known to emplace arrayed slits in an electrophoresis gel by the use of combs the teeth of which penetrate the setting gel. The preferred embodiment of the spacer-comb element 1 in accordance with the present invention has at least two differences.

First, a number, typically three or more and more typically four (as illustrated), arrays of teeth 11 radially extend from an imaginary central axis 12 of the spacer-comb 1, and along the substantial length thereof. Each of the teeth arrays 11 includes a number, normally a different number, of arrayed teeth 111 that suitable to extend into and to emplace slit apertures within the flat sheets of the gel state material (not shown) present in the tray 2.

Second, the trays 2 may be stacked as is taught in the related patent application. In this process the spacer-comb elements 1 serve both as spacers, one tray to the next in a vertical stack, and, with appropriate complimentary features in the form of channels, or grooves 23, 24 on the exterior bottoms of the trays 1, alignment fixtures for the stack. Moreover, as may be noted by consideration of the interaction of a spacer-comb element 1 with either of the recess pairs 21, 22 (or by the interaction of two spacer-comb elements 1 with each of the recess pairs 21, 22), and by the additional interaction of a spacer-comb element 1 with either of the grooves 23, 24 (or by the interaction of two spacer-comb elements 1 with each of the grooves 23, 24), multiple spacer-comb elements 1 serve to align and to position multiple trays 2, and vice versa.

A diagrammatic perspective view of the preferred embodiment of a spacer-comb element.1 in accordance with the present invention in position fitted to the complimentary tray 2 is shown in FIG. 2. The spacer-comb element 1 is positioned transversely across the central reservoir of the tray 2 between the side edge complimentary features 21. In this position one of the teeth arrays 11, and the teeth 111 of this one array, extend downward into the central reservoir of the tray 2. An oppositely disposed one of the teeth arrays 11 extends directly upward from the tray 2. If yet another spacer-comb element 1 (not shown) is positioned between the side edge complimentary features 22, then two lines of support are provided for the placement of yet another tray 2 (not shown) on the top of the two spacer-combs 1, and above the illustrated tray. This top tray (not shown) will be precisely positioned by interaction of its bottom grooves 23, 24 with an upwardly extending one of the teeth arrays 11 of each of the spacer-comb elements 1.

Clearly the trays 2 can possess more than just the illustrated two pairs of top edge complimentary features 21, 22. Clearly the trays 2 can also possess more than just the illustrated two bottom grooves 23, 24. An entire apparatus, or system, of multiple identical trays 2, and an even greater multiple of identical spacer-comb elements 1, is commonly procured, and employed, as suits the particular task at hand in the efficient production of multiple trays of (agarose) gels—replete with arrayed apertures or slits or wells—that are suitable for the conduct of electrophoresis.

A preferred embodiment of a spacer-comb element 1 having four radially extending teeth arrays 11 is shown in two side views (or, alternatively, a "side" and a "top" view, depending upon spatial orientation) in FIGS. 3 and 4. Each of the illustrated four (4) teeth arrays 11 preferably has a different number of teeth than are present in any other of the teeth arrays 11. In the illustrated, preferred, embodiment the preferred four radially extending arrays are evenly angularly located each at 90° of angular separation circumferentially around the central axis. There are respectively 2, 5, 10 and 15 teeth in each of the four (4) teeth arrays 11. The one of the teeth arrays 11 having and presenting two teeth so presents one narrow and one broad tooth. This is so as to emplace in an (agarose) gel solution a broad slit, or aperture, or cavity, or pocket for containing material to be analyzed by electrophoresis, and another, narrower, slit for containing a reference sample—all as is common. More generally there are normally 2, X, 2X and 3X teeth respectively in the preferred four arrays where X is an integer number greater than 2, and where X most commonly equals 5 (as is illustrated) or 6.

The engagement features, or tabs, 13., 14 of the spacer-comb 1 are also most clearly shown in FIGS. 3 and 4. Each of these tabs 13, 14 is preferably formed in (i) a first tab region 13a, 14a that is aligned with the central axis 12 at each end region thereof, that extends beyond each of the four radially extending arrays 11, and that is co-planar with two of the four arrays 11, and as a (ii) a second tab region 13b, 14b that is again aligned with the central axis 12 at each end region thereof, that extends beyond each of the four radially extending arrays 11, and that is co-planar with a remaining two of the four arrays 11. Clearly the first tab region 13a, 14a is perpendicular to the second tab region 13b, 14b.

Notably, the order of the tab regions 13a and 14a, or, equivalently, 13b and 14b, is reversed at the two end regions of the central axis of the spacer-comb 1. This reversal accords that when the spacer-comb element 1 is set on top of the tray 2 spanning the width thereof between the opposing sides at a first side-to-side offset then the first tab regions 13a, 14a will engage the sides of the tray 2, and as a consequence thereof a first selected one of the four teeth arrays 1 will extend downward into the central reservoir of the tray 2, and into the gel material (not shown) contained therein. Alternatively, when the spacer-comb element 1 is set on top of the tray 2 spanning the width thereof between the opposing sides at a second side-to-side offset, then the second tab regions 13b, 14b will engage the sides of the tray 2, and as a consequence thereof a second selected one, perpendicular to the first selected one, of the four teeth arrays 11 will extend downward into the central reservoir of the tray 2, and into the gel material (not shown) contained therein. That particular pair of tab regions—either tab regions 13a and 14a, or else 13b and 14b—that at any one time engage the sides of the tray 2 are, in particular, perpendicular to that particular radially extending teeth array 11 that, at that time extends downward into the central reservoir of the tray 2, and into the gel material (not shown) contained in the reservoir. Basically, any one of the four teeth arrays 1t can be selected to extend downward into the reservoir of the tray 2, and into the gel material (not shown) contained in the reservoir.

A side plan view of a preferred embodiment of a complimentary tray 2, usable with the preferred embodiment of a spacer-comb element 1 in accordance with the present invention, is shown in FIG. 5. A top plan view of the same tray 2 is shown in FIG. 6. Both the top (side wall edge) engagement features 21, 22—the notches 21, 22—and the bottom (surface) engagement features—the grooves 23, 24—may be observed.

Reference to the related patent application, the contents of which are incorporated herein by reference may now prove useful to abet understanding of the method of using multiple spacer-combs 1 and trays 2 to produce multiple trays of gel, each with desired slits. Conversely, and by reference to the discussion given in the BACKGROUND OF THE INVENTION section of this application, the method of use—which is straightforward—may alternatively be attempted to be understood directly from the following explanation.

Clearly, and as explained so far, the spacer-comb element 1 in accordance with the present invention is cooperatively interactive with the tray 2 that both (i) has and defines a central reservoir and sides, and (ii) contains a flat sheet of 10 the gel state material that is suitable to receive samples upon which electrophoresis is performed. Both parts are so cooperatively interactive by virtue of their complimentary engagement features.

In their interaction, a number of the spacer-comb elements 1 in accordance with the present invention are placed between a number of identical trays 2. The trays 2 with intervening spacer-comb elements 1 are vertically stacked. As well as its substantially flat interior reservoir, each tray 2 has and presents an overflow outlet—effectively the short edge lip—from which liquid received into the reservoir will flow out of the reservoir when a predetermined liquid level is reached in the reservoir. Each tray 2 also clearly has a top opening that is, in fact, coextensive with the full size of the tray (although it need not be so). When the trays 2 are stacked, as is illustrated for two trays (only) in FIG. 1, each tray 2 is located so that it may be disposed in position below the overflow outlet of any immediately overlying tray 2 in the vertical stack of these trays 2.

The radially extending teeth arrays 11 of the spacer-comb elements 1 interact with these identical stacked trays 2. First, each of the spacer-comb elements is held and aligned with a one only of its preferred four radially extending teeth arrays 11 extending downward into the central reservoir of the below-located tray 2, and into the gel material contained therein. However, the same engagement also serves to hold, align and maintain the 180° oppositely-directed teeth array 11 in position extending upwards from the below-located tray 2, an into engagement with the bottom features of the immediately overlying tray 2 in the vertical stack of trays 2.

By this construction the spacer-combs with their engagement features serve not only as combs to emplace slit apertures in the gel within an underlying tray, but also as spacers and as rests to align and to support an overlying tray. Everything fits together in a stable fashion, much in the manner of a three-dimensional puzzle.

When the preferred embodiments of the spacer-combs 1 and the trays 2 are so assembled in a vertical stack, or column, then a liquid, typically a heated slurry containing dissolved grains of agarose gel, is poured in the open reservoir of the topmost tray 2. The poured liquid accumulates in the reservoir of the topmost tray 2 until the height of the lowest overflow point, or the overflow lip, of this tray 2 is reached. At this time, the liquid having assumed throughout the reservoir a substantially even depth equal to the height of overflow lip, the liquid will overflow the overflow lip and pour downwards in the open top of the reservoir of the next to topmost tray 2. The reservoir of this next to topmost tray 2 will ultimately become filled, and the liquid will likewise pour from its respective overflow lip into a next lowermost tray 2 The process continues for so long as the liquid is poured, and to such extent as the stack of trays 2 is high, the liquid cascading downwards from tray to tray while filling the reservoir of each tray 2 to a uniform even depth.

The alternating orientation of the overflow lips of the trays 2 in the assembled stack (as illustrated in FIG. 2) clearly makes that the liquid that overflows each tray 2 will fall downward only so far as the immediate next lowermost tray 2, and will be completely caught and contained into the reservoir of this tray.

Considering now the use of the spacer-combs 1, these spacer-combs 1 are interleaved between successive vertically stacked ones of the trays 2. The spacer-combs 1 are held and oriented so that a one teeth array 11 is disposed upwards. This upwardly-disposed teeth array 11 engages next-uppermost tray 2, and is sufficiently strong and stable so as to hold all the overlying trays in the stack.

As in the prior art, the trays 2 are preferably fabricated from U-V transparent acrylic plastic to permit the direct reading of ethidium bromide stains. The acrylic plastic is normally at least 1/32" thick to prevent heat distortion of tray during application of hot agarose solution.

Meanwhile, the spacer-combs 1 may also be fabricated from typically transparent acrylic plastic, normally of 1/8" thickness. The spacer-combs 1 may also be fabricated from polycarbonate, Delrin™ plastic or Teflon™ plastic (Delrin™ and Teflon™ are trademarks of E.I. DuPont de Nemours and Company). The spacer-combs 1 are preferably so fabricated by molding, but may alternatively, conventionally, be fabricated by precision machining. It will be understood that the spacer-combs 1 may have alternative numbers of teeth than that number illustrated in FIGS. 1–4. The spacer-combs 1 are typically fabricated with teeth arrays 11 of 1, 2 (one large well with two marker lanes on each side), 5, 10, 15, 20 teeth in respective widths of 1.0 mm, 2.0 mm or 3.0 mm. Wider spacer-combs 2 used with 20 cm wide versions of the trays 2 typically come with 1,3 (one large well with two marker lanes on each side), 5, 8, 12, 16, 20, 30 or 40 wells at thicknesses of 1.0 mm, 2.0 mm or 3.0 mm.

In accordance with the embodiment of the spacer-comb 1 and trays 2 shown and described, it will be recognized by a practitioner of the mechanical design arts that the construction of vertically stacked array of successive overflowing reservoirs in the manner of an ancient water clock could be realized in many different ways. For example, the required engagement features between spacer-comb 1 and tray 2 (and vice versa) may be formed in many different ways.

Further in accordance with the preceding explanation, variations and adaptations of the each of (i) the vertically stacked trays overflowing liquid congealing into electrophoresis gel, (ii) the optional combination spacer-combs between the trays, and (iii) the spacer-combs (alone) in accordance with the present invention will suggest themselves to a practitioner of the mechanical arts. For example, the trays need not be of uniform size nor depth of fill but could, in accordance with the individual gels desired to be made with the individual trays, could comprise a set of related, and functionally operative, trays. For example, the overflow feature(s) could be physically separated from the trays, and instead incorporated into a multitier free-standing fluid distribution column, much in the manner of a water clock, that would interlock and flow connect a corresponding tier of trays. The trays themselves would then be featureless parallepiped bodies each one of which, when arrayed in the stack or tier, simply flow-communicated with a corresponding level of the fluid distribution column. In this construction the fluid distribution column would incorporate the overflow features, and the resulting downwards cascade of fluid. As the fluid was successively distributed to each level in the fluid distribution column it would flow from that column level into the associated tray. Only when the fluid in all trays had gelled would any, and all, trays be separated from the column, Finally, and for example, once the concept of an in-situ spacer-comb in accordance with the present invention is understood, there are many ways of realizing such a function. A spacer-comb might be rotationally affixed to a disposable tray. Alternatively, one or more spacer-combs could be integrally molded with a tray. The connection between spacer-comb and tray would be frangible, and detachable. After use both spacer-comb and tray could be discarded.

In accordance with these and other possible variations and adaptations of the present invention, the scope of the invention should be determined in accordance with the following claims, only, and not solely in accordance with those particular embodiments within which the invention has been taught.

What is claimed is:

1. A gel electrophoresis element cooperatively interactive with a tray that both (i) has and defines a central reservoir and sides, and (ii) contains a flat sheet of the gel state material that receives samples upon which electrophoresis is performed, for emplacing arrayed slit apertures within flat sheets of a gel state material that itself receives samples upon which electrophoresis may be performed, the element comprising:

a longitudinal central axis;

three or more arrays radially extending about the central axis and extending along a length thereof, each of the arrays comprising a plurality of teeth for extending into and emplacing slit apertures within flat sheets of a gel state material that itself receives samples upon which electrophoresis may be performed into the slit apertures; and engagement features, aligned with the central axis and extending beyond each and all of the pluralities of radially extending arrays at each end region of the central axis, for engaging two opposing sides of the tray while the element is set on top of the tray spanning the width thereof between the opposing sides, the engaging being in a manner so that the element is stably held with the arrayed of teeth of one only of its plurality of arrays extending downward into the central reservoir of the tray, and into the gel material contained therein.

2. The element according to claim 1
wherein at least two of the three or more radially extending arrays comprise pluralities of teeth that are different in number.

3. The element according to claim 1
wherein there are four radially extending arrays.

4. The element according to claim 3
wherein the plurality of teeth of each of the four arrays are different in number from the plurality of teeth any of the other three arrays.

5. The element according to claim 3
wherein the four radially extending arrays are evenly angularly located each at 90° of angular separation circumferentially around the central axis.

6. The element cooperatively interactive with a tray according to claim 1
wherein there are four radially extending arrays each located at 90° of angular separation circumferentially around the central axis;
and wherein the engagement features comprise:
a first tab region, aligned with the central axis at each end region thereof and extending beyond each of the four radially extending arrays, that is co-planar with two of the four arrays; and
a second tab region, aligned with the central axis at each end region thereof and extending beyond each of the four radially extending arrays, that is co-planar with a remaining two of the four arrays;
wherein the first tab region is perpendicular to the second tab region;
wherein the order of the tab regions is reversed at the two end regions of the central axis of the element, this reversal making that
(i) when the element is set on top of the tray spanning the width thereof between the opposing sides at a first side-to-side offset then the first tab regions will engage the sides of the tray, and as a consequence thereof a first selected one of the four arrays will extend downward into the central reservoir of the tray, and into the gel material contained therein, and
(ii) when the element is set on top of the tray spanning the width thereof between the opposing sides at a second side-to-side offset then the second tab regions will engage the sides of the tray, and as a consequence thereof a second selected one, perpendicular to the first selected one, of the four arrays will extend downward into the central reservoir of the tray, and into the gel material contained therein.

7. The element cooperatively interactive with a tray according to claim 6
wherein the tab regions engaging the sides of the tray at any one time are perpendicular to the radially extending array then extending downward into the central reservoir of the tray, and into the gel material contained therein.

8. A number of gel electrophoresis elements cooperatively interactive with a number of identical trays that are used to prepare in each tray from a liquid material poured into the tray a flat sheet of a gel state material that receives samples upon which electrophoresis may be performed, each tray including a tray body vertically stacked with a number of other trays in a vertical stack, the tray body having and defining a interior reservoir, an overflow outlet from which liquid received into the reservoir will flow out of the reservoir when a predetermined liquid level is reached in the reservoir, and a top opening located so that it is disposed in position below the overflow outlet of any immediately overlying tray in the vertical stack of trays, each element comprising:

a longitudinal central axis;
four radially extending arrays each located at 90° of angular separation circumferentially around the central axis and extending along a length thereof, each of the arrays comprising a plurality of teeth for extending into and emplacing slit apertures within flat sheets of a gel state material that itself receives samples upon which electrophoresis may be performed into the slit apertures;

engagement features, aligned with the central axis and extending beyond each and all of the pluralities of radially extending arrays at each end region of the central axis, for engaging two opposing sides of the tray while the element is set on top of the tray spanning the width thereof between the opposing sides, the engaging being in a manner so that the element is stably held with the arrayed of teeth of one only of its plurality of arrays extending downward into the central reservoir of the tray, and into the gel material contained therein;

wherein the engagement features serving to hold and maintain the teeth of one only of the four arrays extending downward into the central reservoir of the tray, and into the gel material contained therein, also serve to hold and maintain the 180° oppositely directed array extending upwards from the tray so as to serve as a spacer and as a rest for an immediately overlying tray in the vertical stack of trays;

wherein the elements with their engagement features serve not only as combs to emplace slit apertures in the gel within an underlying tray, but also as a spacer and as a rest to support an overlying tray.

9. A gel electrophoresis apparatus for preparing from a liquid material a flat sheet of a gel state material having and defining an array of wells each of which receives a sample upon which electrophoresis may be performed, the apparatus comprising:

a tray having a base and sides defining an interior reservoir; and
a spacer-comb element comprising:
a longitudinal central axis; and
four radially extending arrays each located at 90° of angular separation circumferentially around the central axis and extending along a length thereof, each of the arrays comprising a plurality of teeth extending into and emplacing slit apertures within flat sheets of a gel state material that receives samples upon which electrophoresis may be performed;

wherein the spacer-comb element overlies the reservoir of the tray between the sides of the tray so that its teeth extend into the reservoir, therein to establish within the reservoir an array of small volumes into which volumes any liquid poured into the reservoir cannot enter;

wherein, when a liquid material is poured into the tray while the member is in place at least partially overlying the tray's reservoir, and after the liquid material is allowed to gel to a gel state, a separation of the member from the tray leaves an array of voids in the gel state material that is within the tray's reservoir, the voids receiving samples upon which electrophoresis transpires.

10. The apparatus according to claim 9 wherein the tray comprises:

a tray body vertically stacked with a number of other trays in a vertical stack, the tray body having and defining an interior reservoir, an overflow outlet from which liquid received into the reservoir will flow out of the reservoir when a predetermined liquid level is reached in the reservoir, and a top opening located so that it is disposed in position below the overflow outlet of any immediately overlying tray in the vertical stack of trays and wherein the spacer-comb element comprises:

features engaging the sides of the tray so as to hold and maintain the comb stable, with the teeth of one only of its four arrays extending downward into the central reservoir of the tray and into the gel material contained therein, and also with a one array that is 180° oppositely directed extending upwards from the tray so as to serve as a spacer and as a rest for an immediately overlying tray in the vertical stack of trays;

wherein the spacer-comb element serves not only to emplace slit apertures in the gel within the reservoir of an underlying tray, but also as a spacer and as a rest to support an overlying tray, and is thus called a spacer-comb.

* * * * *